US012767938B2

(12) United States Patent
Forssmann et al.

(10) Patent No.: US 12,767,938 B2
(45) Date of Patent: Oct. 20, 2026

(54) POLYPEPTIDE FOR THE THERAPY OF GLOMERULAR KIDNEY DISEASE AND ANALYSIS OF THE COURSE AND PROGNOSIS OF DEPENDENT SYNDROMES

(71) Applicants: PHARIS BIOTEC GmbH, Hanover (DE); FRIEDRICH-ALEXANDER-UNIVERSITÄT, Erlangen (DE)

(72) Inventors: Wolf-Georg Forssmann, Hanover (DE); Mario Schiffer, Erlangen (DE)

(73) Assignee: FRIEDRICH-ALEXANDER-UNIVERSITÄT, ERLANGE NÜRNBERG, Erlangen (DE)

( * ) Notice: Subject to any disclaimer, the term of this patent is extended or adjusted under 35 U.S.C. 154(b) by 580 days.

(21) Appl. No.: 17/912,181

(22) PCT Filed: Mar. 16, 2021

(86) PCT No.: PCT/EP2021/056610
§ 371 (c)(1),
(2) Date: Sep. 16, 2022

(87) PCT Pub. No.: WO2021/185798
PCT Pub. Date: Sep. 23, 2021

(65) Prior Publication Data
US 2023/0144625 A1 May 11, 2023

(30) Foreign Application Priority Data
Mar. 18, 2020 (EP) .................................... 20163836

(51) Int. Cl.
*C12N 9/22* (2006.01)
*A61K 38/46* (2006.01)
*G01N 33/50* (2006.01)

(52) U.S. Cl.
CPC .............. *C12N 9/22* (2013.01); *A61K 38/465* (2013.01); *C12Y 301/27005* (2013.01); *G01N 33/5044* (2013.01); *G01N 2333/705* (2013.01); *G01N 2333/922* (2013.01)

(58) Field of Classification Search
CPC ............................... C12N 9/22; A61K 38/465; C12Y 301/27005; G01N 33/5044; G01N 2333/705; G01N 2333/922
See application file for complete search history.

(56) References Cited

U.S. PATENT DOCUMENTS

| | | | |
|---|---|---|---|
| 8,841,416 B2 * | 9/2014 | Ledbetter ................ | A61P 15/00 424/193.1 |
| 2014/0038203 A1 | 2/2014 | Arthur et al. | |

FOREIGN PATENT DOCUMENTS

| | | |
|---|---|---|
| JP | 2015-156821 A | 9/2015 |
| WO | 2009-048909 A1 | 4/2009 |
| WO | 2010-091231 A1 | 8/2010 |
| WO | 2011-015446 A1 | 2/2011 |
| WO | 2011-109830 A1 | 9/2011 |
| WO | 2016-037985 A1 | 3/2016 |
| WO | 2018-115305 A1 | 6/2018 |

OTHER PUBLICATIONS

Moore, Stanford, and William H. Stein. "Chemical structures of pancreatic ribonuclease and deoxyribonuclease." Science 180.4085 (1973): 458-464. (Year: 1973).*
Ronconi, Elisa, et al. "Regeneration of glomerular podocytes by human renal progenitors." Journal of the American Society of Nephrology 20.2 (2009): 322-332. (Year: 2009).*
International Search Report from corresponding PCT Application No. PCT/EP2021/056610 dated Jun. 15, 2021.

* cited by examiner

*Primary Examiner* — Robert J Yamasaki
*Assistant Examiner* — Trevor Kane
(74) *Attorney, Agent, or Firm* — Christensen, Fonder Dardi PLLC; Peter S. Dari; Elizabeth A. Gallo

(57) ABSTRACT

A pharmaceutical composition containing human ribonuclease 1 is disclosed. The molecule according to the invention (or the analogous variants) is suitable for use as a medicament for therapy of renal diseases of various aetiologies. The drug according to the invention causes regeneration of glomerular podocytes. The molecule according to the invention can be further used by analytical determination of blood concentration as a marker of disease progression of renal syndromes and for prognosis and prevention of renal insufficiency as a valuable factor of laboratory medicine.

8 Claims, 2 Drawing Sheets

Figure 1:
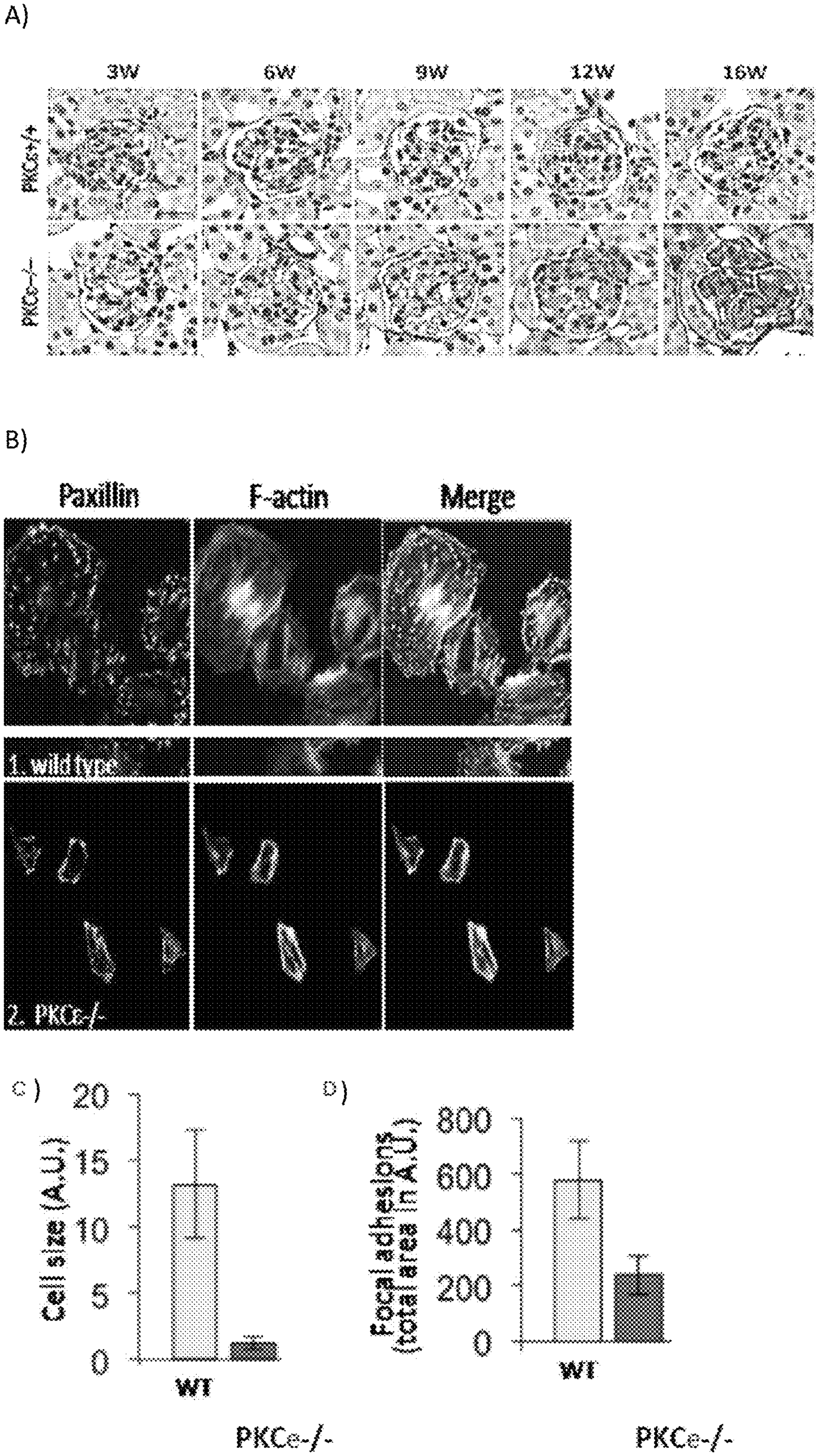

Specification includes a Sequence Listing.

POLYPEPTIDE FOR THE THERAPY OF GLOMERULAR KIDNEY DISEASE AND ANALYSIS OF THE COURSE AND PROGNOSIS OF DEPENDENT SYNDROMES

CROSS REFERENCE TO RELATED APPLICATIONS

This application is a National Stage filing of PCT Application No. PCT/EP2021/056610 filed Mar. 16, 2021, entitled "Polypeptide or the Therapy of Glomerular Kidney Disease and Analysis of the Course and Prognosis of Dependent Syndromes", which claims priority to European Patent Application No. 20163836.8, filed Mar. 18, 2020.

The present invention relates to a pharmaceutical composition comprising a polypeptide useful for the therapy of renal disease. It is also an object of the invention to provide an in vitro method for diagnosing and monitoring the progression of renal disease by determining the level of ribonuclease in body fluids or tissues of a patient.

Acute kidney failure can progress to a terminal stage at any time, leading to complete loss of kidney function without extensive therapy such as renal replacement procedures (hemofiltration, hemodialysis). Acute kidney failure (AKF) is one of the most common causes of death in industrialized nations (over 10%), with developments particularly pronounced in underlying diseases such as type 2 diabetes mellitus, hypertension due to lack of exercise and malnutrition, as well as causes such as ingestion of toxic substances (smoking, alcohol, medications) and further chronic, inflammations and infections of the kidneys, narrowing of the urinary tract and congenital kidney diseases pass into AKF or end in chronic kidney disease (CKD).

Thus, the diagnosis of the various renal failures, monitoring the course of the disease, prophylaxis of the disease forms and their specific therapy is an extraordinary challenge (unmet need).

Chronic kidney disease (CKD) affects approximately 10% of the Western world population (Brück K., Stel V. S., Gambaro G. 2016; CKD Prevalence Varies across the European General Populations. JASN 27 (7) 2135-2147). The majority of kidney diseases that progress to CKD start in the glomerulus, the filtration unit of the kidney. This is a consequence of the limited regenerative capacity of the glomerulus due to the limited ability of glomerular podocytes to self-renew. Podocytes are an essential component of the three-layer filtration barrier of the kidney (Tryggvason, K. and Pettersson; E. 2003; Causes and consequences of proteinuria: the kidney filtration barrier and progressive renal failure. J Intern Med 254, 216-224). Podocyte function is regulated by a highly specialized cellular function, the formation of a signal-active cell-cell junction called the slit diaphragm. This modified adherence junction forms between the podocytic foot processes. The foot processes are specialized cell extensions, with finely regulated cytoskeletal structures that are subject to steady assembly and disassembly, regulating the assembly and disassembly of cellular focal junctions (Sever S and Schiffer M. Actin dynamics at focal adhesions: a common endpoint and putative therapeutic target for proteinuric kidney diseases, Kidney Int. 2018 June; 93(6):1298-1307). The cytoskeleton of podocytes is constructed by various proteins. It is the basic requirement for the stabilization and construction of the slit membrane. If this cytoskeleton is affected, for example by mutations or toxins, this affects the functionality of the slit membrane, which in almost all cases leads to excessive excretion of proteins via the urine (proteinuria). To date, no specific therapeutic options are available for such "podocytopathies". In general, these diseases are treated with immunosuppressive drugs. Whether this therapy induces specific effects on the podocytes or triggers secondary positive effects via other mechanisms (possibly via the induction of ribonucleases) remains open.

In general, proteinuria poses a significant mortality and morbidity risk. Individuals with increased urinary excretion of proteins such as albumin (albuminuria) are at increased risk of progressive loss of renal function, including renal failure requiring dialysis. If kidney function is still given, however, mortality increases with increasing protein excretion, as does the risk of suffering a heart attack. Thus, proteinuria represents an independent risk factor for cardiovascular diseases.

Differentiated podocytes are no longer capable of regenerative mitotic cell division after completion of organogenesis (Rennke, H. G. 1994; How does glomerular epithelial cell injury contribute to progressive glomerular damage? Kidney Int Suppl 45, p 58-63). In the disease situation, cell-cell contacts are initially lost and slit membrane proteins are only detectable at a reduced level. As long as the cells are still present, there is still a potential to rebuild these cell-cell junctions with the right therapy. In prolonged disease states, however, the podocytes die and with them the entire glomerulus and the subsequent nephron perish.

Thus, a problem underlying the invention is to provide a compound capable of restoring podocyte differentiation and reconstruction, promoting regeneration and formation of cellular foot processes, and alleviating or curing associated renal diseases.

Surprisingly, it was found that pancreatic ribonuclease can serve as a modulator in disturbed cytoskeletal structure of podocytes, especially in differentiation disorders.

According to the invention, the polypeptide can be used as a medicine in the treatment of diseases of renal function caused by differentiation disorders and reconstruction of the podocyte structure and its proliferation. This applies to all renal diseases associated with protein excretion.

In addition to the complete polypeptide ribonuclease, its derivatives, variants and fragments are also suitable as medicine, provided that they exhibit activity comparable to that of native ribonuclease in the regeneration of podocytes in the event of disease.

In one embodiment the ribonuclease has at least 70%, in particular at least 80%, in particular at least 90%, in particular at least 95% sequence identity with the polypeptide of SEQ ID No. 1.

The ribonuclease according to the invention may be present in a substantially aqueous solution, in particular in aqueous solution with pharmaceutical excipients.

In particular, the ribonuclease according to the invention may be present as a formulation to be administered parenterally.

The ribonuclease may preferably be present in an amount of at least one functional unit having ribonuclease activity per dosage unit.

It is also an object of the invention to provide a ribonuclease for the treatment of renal diseases, wherein the ribonuclease is preferably human, porcine or bovine pancreatic ribonuclease, preferably human pancreatic ribonuclease. The ribonuclease preferably has at least 70%, in particular at least 80%, in particular at least 90%, in particular at least 95% sequence identity with the polypeptide of SEQ ID No 1. Especially preferred is has the SEQ ID No. 1.

The ribonuclease to be used according to the invention promotes the regeneration of glomerular podocytes and is therefore particularly suitable for the treatment of renal diseases.

It is also an object of the present invention to use pancreatic ribonuclease, in particular human pancreatic ribonuclease or hRNase 1 to identify ribonuclease receptors of renal cells in an assay. Corresponding assay procedures for the identification of targets of ligands are known to the skilled person. In particular, labelled pancreatic ribonucleases can be used.

It is also an object of the present invention to use pancreatic ribonuclease, in particular human pancreatic ribonuclease or hRNase 1, to identify substrates of pancreatic ribonuclease that are causally related to podocyte degeneration. Corresponding screening methods are familiar to those skilled in the art.

Furthermore, it is an object of the present invention to provide an ex vivo method for the removal of substrates of pancreatic ribonuclease that are causally related to podocyte degeneration, in particular extracorporeal procedures such as hemodialysis, hemofiltration, hemodiafiltration, peritoneal dialysis, plasma exchange treatment, or treatment with nonspecific filters or specific ribonuclease-containing filter units that remove or inactivate the substrates from the blood.

It is also an object of the invention to provide an in vitro diagnostic method that uses the quantitative presence of the polypeptide used in accordance with the invention, in particular ribonuclease, for example human ribonuclease, as an indicator of the severity of kidney degeneration or the reversibility of kidney function. Determining the concentration of ribonuclease during the course of the disease is important, among other things, for considering the relevance of the disease.

Ribonuclease, in particular human pancreatic ribonuclease, for example human pancreatic ribonuclease 1 is measurable by various analytical methods of peptide chemistry, for example:

1. Immunochemical by techniques such as ELISA etc.
2. Different techniques of gel chromatography,
3. Capillary electrophoresis, thin layer chromatography
4. HPLC display with reverse phase or affinity chromatography
5. quantitative mass spectrometry LC-MS or quadrupole, etc.

FIG. 1: Phenotype of the PKCε-knockout.

Figure 2:
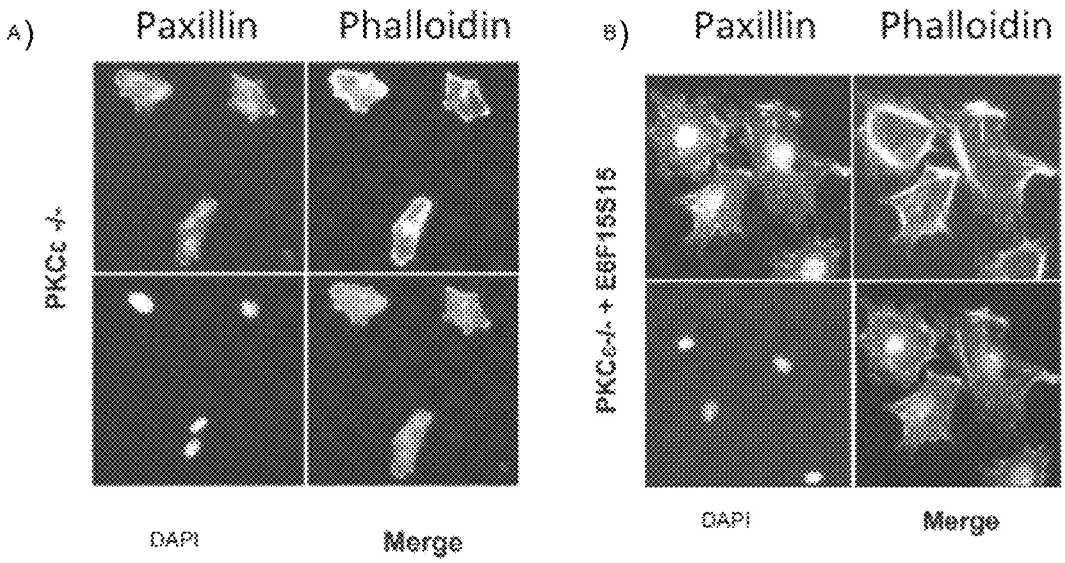

FIG. 2: Fractions containing hRNase1 ameliorate actin cytoskeleton dysregulation in PKCε-deficient podocytes.

Figure 3:
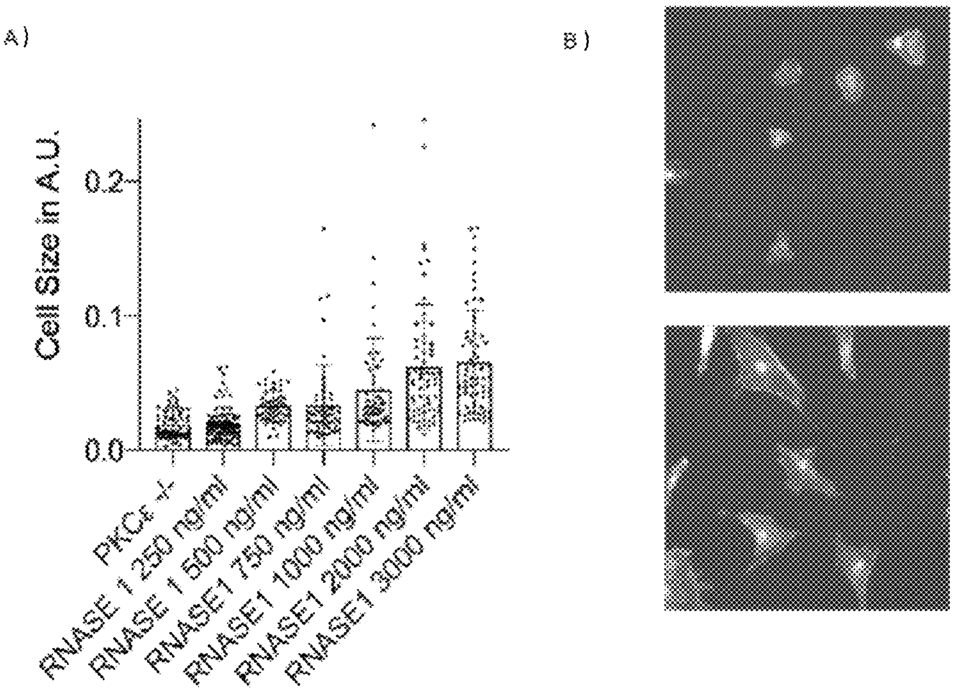

FIG. 3: Illustration of the rescue effect of recombinant human RNAse 1 action on the cell structure of PKCε-deficient podocytes.

The invention is explained in more detail below.

Ribonucleases are hydrolases belonging to group III of the EC classification of enzymes, which hydrolytically cleave the ester cleavage between the 5'-phosphate group of a nucleotide and the 3'-hydroxyl group of an adjacent one within an RNA molecule. Two classes of ribonucleases can be distinguished.

RNase I (pancreatic RNase): cleavage only behind pyrimidine nucleotides, RNase I is inhibitable by heparin.

RNase II (plant RNase): cleavage behind purine and pyrimidine nucleotides. The present invention is based on the surprising discovery that the polypeptide serves as a modulator in disturbed cytoskeletal structure of podocytes, especially in differentiation disorders. The polypeptide can be used as a drug in the treatment of renal function diseases caused by differentiation disorders and reconstruction of podocyte structure and its proliferation. Scientific literatune also discusses a function of the ribonuclease family as a receptor ligand (Wang et al. Journal of Biomedical Science (2018) 25:83). hRNase 5 is described there as a ligand of EGFR RTK. Thus, a binding of RNase superfamily members to proteins of the receptor tyrosine kinase family (RTK or RYK) is likely.

Podocytes are highly specialized cells that play an essential role in the filtration of blood in the renal corpuscles. These cells are terminally differentiated, i.e. they can no longer divide and thus regenerate or replace damaged podocytes. In most kidney diseases, a progressive loss of podocytes is observed, and despite their terminal differentiation, these cells re-enter the cell cycle, but cannot go through it to cell division and instead perish.

The effect of the polypeptide of the present invention can be detected by a bioassay. The corresponding assay is explained in more detail in the examples.

The medicament according to the invention contains in particular human pancreatic ribonuclease. The amino acid sequence of the human pancreatic ribonuclease polypeptide contained in the drug according to the invention, including the signal peptide, is as follows according to the entry in the uniprot database https://www.uniprot.org/uniprot/P07998#sequences (SEQ ID No. 2):

*MALEKSLVRLLLLLVLILLVLGWVQPSLG*KESRAKKFQRQ
MDSDSSPSSSSTYC-NQMMRRRN-MTQGRCKPVNTFVHE
PLVDVQNVCFQEKVTCKNGQGNCYKSNSSMHITDCRLTN
GSRYPNCAYRTSPKERHIIVACEGSPYVPVHFDASVEDS
T

Underlined are three potential N-glycosylation sites, two of which are occupied.

The amino acids in italics in the above sequence represent the signal peptide.

(SEQ ID No. 3)
MALEKSLVRLLLLLVLILLVLGWVQPSLG

The active polypeptide is (SEQ ID No. 1):

KESRAKKFQRQMDSDSSPSSSSTYCNQMMRRRNMTQGRCK-
PVNTFVHEPLVDVQNVCFQEKVTCKNGQGNCYKSNSSMHIT
DCRLTNGSRYPNCAYRTSPKERHIIVACEGSPYVPVHFDAS
VEDST

Ribonuclease was originally identified in hemofiltrate fractions as an effective agent for podocyte regeneration in a bioassay. Although isolation of human pancreatic ribonuclease from hemofiltrate is possible in principle, recovery of the polypeptide is also possible by total synthesis according to Merrifield. Preferably, however, the polypeptide is provided by recombinant methods and expression in suitable systems. In this context, the expression of the corresponding polynucleotides encoding the pancreatic ribonuclease is recommended in biological systems, in particular eukaryotic cells, which post-translationally provide the expressed polypeptide with the human glycosylation pattern. However, depending on the cell culture used to express the polypeptide, other mammalian pancreatic ribonucleases expressed from cells of mammals can also be used, for example those from primates such as monkeys, chimpanzees, macaques and gorillas but also from non-primates such as mice, rats, guinea pigs, hamsters, rabbits, cows, horses, sheep, goats and pigs.

In the sense of the invention, pancreatic ribonuclease polypeptides are also those that are functional equivalents of human pancreatic ribonuclease, i.e. have a similar amino acid sequence and are capable of acting as modulators of podocytes.

In one embodiment of the medicament according to the invention, the latter may contain a ribonuclease which has at least 70%, in particular at least 80%, in particular at least 90%, in particular at least 95% sequence identity with the polypeptide of SEQ ID No. 1.

In another embodiment of the polypeptide for use as a medicament, the polypeptide may also be a variant of pancreatic ribonuclease. Variants are fragments of the polypeptide which typically have at least 5-20 flanking amino acids on either side of the regions acting on podocyte regeneration. Fragments in the sense of the invention typically comprise at least 25, 50, 75, 100 or 150 amino acids.

However, pancreatic ribonuclease variants also include polypeptides that are essentially identical to the native amino acid sequence of pancreatic ribonuclease. These variants also include polypeptides with changes to the amino acid sequence of the native polypeptide such as the deletions, insertions and or substitutions.

The term "deletion" refers to the absence of one or more amino acid residues in the polypeptide. The term "insertion" means the addition of one or more amino acids in the polypeptide in question. The term "substitution" means the replacement of one or more amino acid residues with other amino acids in the polypeptide. Typically, such changes are conservative in nature whereby the activity of the variant polypeptide remains substantially similar or the same compared to the native polypeptide. In the case of a substitution, the amino acid replacing the other amino acid in the native polypeptide usually has similar structural and or chemical properties. Insertions and deletions typically involve ranges of 1-5 amino acids, although this is dependent on the location of the insertion, so even more amino acids can be inserted or removed without unduly altering the function of the native polypeptide. Variations of the native polypeptide can be introduced, particularly at the polynucleotide level, for example, by the well-established methods of site-directed mutagenesis [site-directed mutagenesis (Carter, et al. (1986) Nucl. Acids Res. 13:4331; Zoller et al. (1987) Nucl. Acids Res. 10: 6487), cassette mutagenesis (Wells et al. (1985) Gene 34: 315), restriction selection mutagenesis (Wells, et al. (1986) Philos. Trans. R. Soc. London SerA 317: 415), and PCR mutagenesis (Sambrook, et al. (1989) Molecular Cloning, Cold Spring Harbor Laboratory Press)].

Pancreatic ribonuclease variants also include modified forms of the polypeptide as well as its derivatives. Modified pancreatic ribonuclease are polypeptides in which one or more amino acids of the native sequence have been altered such that a non-naturally occurring amino acid residue is present in the polypeptide chain. Such modifications are generally performed during or after protein translation and include, for example, phosphorylation, glycosylation, sulfonation, cross-linking, acylation, hesylation, PEGylation, or proteolytic cleavage. Polypeptides obtained by the aforementioned modifications, which may also be fragments of the polypeptide ribonuclease to be used according to the invention, are also referred to as derivatives. Typically, amino acid exchanges can be made in a conservative manner A conservative exchange is a mutation in which one codon is replaced by another. This involves coding for a different amino acid, but one that is chemically related to the original amino acid, such as glycine with alanine or threonine with serine. A non-conservative substitution, on the other hand, occurs when the original codon is replaced by a codon encoding an amino acid with different chemical properties, for example glycine with lysine.

The terms "identical" or percent "identical" in the context of two or more polypeptides refers to two or more sequences or subsequences that are the same or have a certain percentage of amino acids that are identical when compared and aligned, using a sequence comparison algorithm, for maximum match. Optimal alignment for comparing sequences can be performed using, for example, the following algorithms Local Homology Alignment by Smith &Waterman, Adv. Appl. Math. 2: 482 (1981); Homology Alignment Algorithm of Needleman & Wunsch, J. Mol. Biol. 48: 443 (1970), Pearson & Lipman, Proc. Nat'l. Acad. Sci. USA 85: 2444 (1988), (GAP, BESTFIT, FASTA, and TFASTA in Wisconsin Genetics Software Package, Genetics Computer Group, 575 Science Dr., Madison, WI), but also visual examination [compare, Current Protocols in Molecular Biology, (Ausubel, F. M. et al., eds.) John Wiley & Sons, Inc., New York (1987-1999, including Supplement 46 (April 1999)].

The expression "substantially identical" or similar expressions used in connection with two polypeptides refers to two or more sequences or subsequences which have at least 70%, in particular at least 80%, in particular at least 90%, in particular at least 95% sequence identity when these are compared and aligned for maximum match using a sequence comparison algorithm. Substantial identity exists in particular when a sequence region having a length of at least 40-60 amino acids, in particular 60-80 amino acids, in particular more than 90-100 amino acid residues, and in particular is substantially identical over the entire length of the amino acid sequence of the native polypeptide.

The medicament according to the invention can be after in a substantially aqueous solution, in particular in aqueous solution with pharmaceutical excipients.

The excipients can be added individually or in combinations not only to the polypeptide, but also to a final formulation. The excipients can be added at various points in the galenic preparation of the medicament.

It may be advisable to stabilize the polypeptide against aggregation or oligomerization. If necessary, a bacteriostatic agent, such as benzyl alcohol, a surfactant, such as Tween 20, an isotonic agent, such as mannitol, one or more stabilizing amino acids, such as lysine or arginine, and an antioxidant may also be added to the formulation.

In particular, the medicament according to the invention contains ribonuclease in a formulation suitable for parenteral administration.

The medicament according to the invention preferably contains the ribonuclease in an amount of at least one functional molecule per dosage unit.

It is also an object of the invention to provide a ribonuclease for the treatment of renal diseases, wherein the ribonuclease is preferably human pancreatic ribonuclease. The ribonuclease preferably has at least 70%, in particular at least 80%, in particular at least 90%, in particular at least 95% sequence identity with the polypeptide of SEQ ID No 1.

The ribonuclease to be used according to the invention promotes the regeneration of glomerular podocytes and is therefore particularly suitable for the treatment of renal diseases.

Fragments of ribonuclease, which may be present in the medicament according to the invention, are typically obtained by cleavage of the polypeptide chain of ribonuclease. Methods for fragmentation by cleavage of the polypeptide chain are known to the skilled person.

For example, polypeptides can be cleaved by enzymes known as proteases. Depending on whether the proteases cleave polypeptides (proteins) within the amino acid chain or at the end, a distinction is made between proteinases (also called endopeptidases). They cleave proteins within the amino acid chain. In most cases, they recognize specific sequence segments within a protein at which they can attack and cleave there.

On the other hand, exoproteases (also called exopeptidases) cleave individual amino acids from the ends of the protein. In contrast to proteinases, they primarily break down smaller peptides and not proteins. A distinction is made between:

Carboxypeptidases, which cleave amino acids from the carboxyl end (C-terminus), and aminopeptidases, which cleave amino acids from the amino end (N-terminus).

Specific proteases cleave the peptide bond between two specific amino acids; in some cases, they also recognize more than one substrate. These proteases are used, for example, to study the relatedness of proteins, to prepare proteins for sequencing, or to isolate active domains of a protein. Some examples of such proteases are shown in the table:

TABLE 1

Specific proteases and their properties

| Protease | Specificity of cleavage |
|---|---|
| Pepsin | Phe⇓X, Leu⇓X<br>and pairs of nonpolar amino acids |
| Trypsin | Arg⇓X, Lys⇓X |
| Chymotrypsin | Tyr⇓X, Phe⇓X, Trp⇓X |
| Thrombin | Arg⇓X |
| Thermolysin | X⇓Leu, X⇓Phe, other nonpolar residues |
| Endoproteinase Lys-C | Lys⇓X |
| Endoproteinase Glu-C | Glu⇓X (partly also Asp⇓X) |
| Endoproteinase Arg-C (clostripain) | Arg⇓X |

In contrast to specific proteases, non-specific proteases cleave the peptide chain before or after a whole series of amino acids and thus generate much smaller cleavage pieces. Some examples of such non-specific proteases are shown in the following table 2:

TABLE 2

Non-specific proteases and their properties

| Protease | Specificity of cleavage |
|---|---|
| alkaline protease | Phe⇓X, Leu⇓X, Val⇓X,<br>Ile⇓X, Trp⇓X, Tyr⇓X |
| Papaine | Arg⇓X, Lys⇓X, Phe⇓X |
| Proteinase K | wide substrate spectrum |

For proteolytic analysis of peptides, certain chemicals can be used in addition to proteases. Bromocyanine (BrCN) is the most important reagent of this type and cleaves proteins on the C-terminal side of methionine residues. Peptidyl-homoserine lactone is formed in the process. The resulting peptide fragments can then be separated in the polyacrylamide gel and visualized by staining.

TABLE 3

Typical reagents for chemical proteolysis and their properties

| Reagent | Specificity of cleavage |
|---|---|
| Bromcyan | Met⇓X |
| partial acid hydrolysis | Asp⇓Pro |
| Hydroxylamine | Asn⇓Gly |

A special case of proteolysis is the so-called limited proteolysis. In contrast to total hydrolysis, protein digestion is not complete in this method, but takes place under precisely defined reaction conditions (proteolysis thus proceeds in a limited manner). In the globular regions of a native protein, the peptide bonds are much less exposed than the peptide bonds on the surface of the protein. This means that if a protease is exposed for a short time, or if the protease concentration is very low, the individual protein domains may be separated first before the protease reaches cleavage sites further inside. Thus, limited proteolysis is performed with a protease dilution and/or suboptimal reaction conditions and stopped after a short time. In this method, the protein is proteolytic ally cleaved in its native form (and not after denaturation); this sometimes has consequences for the choice of protease. For example, if the protein requires EDTA for optimal stability, a metalloprotease cannot be used for digestion.

Further information on protein analysis and procedures for proteolytic cleavage of polypeptides can be found in the textbook "Arbeitsmethoden der Biochemie" by Alfred Pingoud, Claus Urbanke, Walter de Gruyter, for example chapter 5.1.6.

Kidney disease may be selected, in particular, from the group consisting of: Diabetic nephropathy, nephrotic syndrome, nephritic syndrome, toxic side effects of other therapies, glomerular diseases such as membranous glomerulonephritis, focal segmental glomerulosclerosis (FSGS), IgA nephropathy, IgM nephropathy, membranoproliferative glomerulonephritis, minimal change disease, hypertensive nephrosclerosis, and interstitial nephritis, Fabry disease, infections, aminoaciduria, Fanconi syndrome, heavy metal poisoning, sickle cell disease, hemoglobinuria, multiple myeloma, myoglobinuria, organ rejection, especially renal transplant rejection and recurrent renal transplant disease, preeclampsia, acute renal failure, and genetic podocytopathies.

A major function of ribonuclease is to cleave RNA molecules. The mechanism of action underlying podocyte regeneration in response to ribonuclease administration is not known. Without being bound to an explanation of the effect, degradation of RNA molecules caused by ribonuclease, particularly human pancreatic ribonuclease 1, which is associated with the aetiology of renal disease associated with podocyte degeneration, may cause podocyte regeneration to occur. In addition to or even instead of administration of the drug according to the invention, removal of the RNA degraded by the ribonuclease could also contribute to podocyte regeneration. Consequently, it is also an object of the present invention to carry out an in vitro removal of undegraded RNA, in particular an in vitro method for the removal of substrates of the pancreatic ribonuclease, which are in a causal context with the degeneration of podocytes. Suitable methods include, in particular, extracorporeal procedures such as hemodialysis, hemofiltration, hemodiafiltration, peritoneal dialysis, cytosorb and other non-specific filters, and plasma exchange treatments.

In hemodialysis, the patient's blood is pumped through the blood compartment of a dialyzer, exposing it to a partially permeable membrane. The dialyzer is composed of thousands of tiny hollow synthetic fibers. The fiber wall acts as the semipermeable membrane. Blood flows through the fibers, dialysis solution flows around the outside of the fibers, and water and wastes move between these two solutions. The cleansed blood is then returned via the circuit back to the body. Ultrafiltration occurs by increasing the hydrostatic pressure across the dialyzer membrane This usually is done by applying a negative pressure to the dialysate compartment of the dialyzer. This pressure gradient causes water and dissolved solutes to move from blood to dialysate and allows the removal of several litres of excess fluid during a typical 4-hour treatment.

Hemofiltration is a similar treatment to hemodialysis, but it makes use of a different principle. The blood is pumped through a dialyzer or "hemofilter" as in dialysis, but no dialysate is used. A pressure gradient is applied; as a result, water moves across the very permeable membrane rapidly, "dragging" along with it many dissolved substances, including ones with large molecular weights, which are not cleared as well by hemodialysis. Salts and water lost from the blood during this process are replaced with a "substitution fluid" that is infused into the extracorporeal circuit during the treatment.

Hemodiafiltration is a combination of hemodialysis and hemofiltration, thus used to purify the blood from toxins when the kidney is not working normally and also used to treat acute kidney injury (AKI).

In peritoneal dialysis, a sterile solution containing glucose (called dialysate) is run through a tube into the peritoneal cavity, the abdominal body cavity around the intestine, where the peritoneal membrane acts as a partially permeable membrane. This exchange is repeated 4-5 times per day; automatic systems can run more frequent exchange cycles overnight.

Using cytokine-adsorbing columns (cytosorbs) or other non-specific filters involves channeling the patient's blood through a cartridge containing millions of minuscule polymer beads which trap toxins and inflammatory proteins. For this reason, the technology can only be used in conjunction with an additional blood pump system, like a dialysis machine or a heart-lung machine.

Plasmapheresis is the removal, treatment, and return or exchange of blood plasma or components thereof from and to the blood circulation. It is thus an extracorporeal therapy (a medical procedure performed outside the body). Exchange plasmaphoresis includes removing blood plasma and exchanging it with blood products to be donated to the recipient. This type is called plasma exchange (PE, PLEX, or PEX) or plasma exchange therapy (PET). The removed plasma is discarded and the patient receives replacement donor plasma, albumin, or a combination of albumin and saline (usually 70% albumin and 30% saline).

In one embodiment of the extracorporeal method according to the invention, the body fluid to be purified can be contacted with ribonuclease immobilized on a carrier after its removal. In this process, the ribonucleic acids associated with the aetiology of the renal disease are degraded. In another embodiment, the RNA fragments may be removed from the body fluid by extracorporeal procedures.

Another object of the present invention arises from the discussion in the scientific literature that ribonuclease can be considered as ligands for receptors. In particular, the binding of ribonuclease to receptor tyrosine kinases supports this assumption. The binding of ribonuclease, in particular human pancreatic ribonuclease 1, to a corresponding target, probably a receptor from the receptor tyrosine kinase (RTK) family, triggers a signaling cascade, as a result of which podocytes regenerate.

By means of the finding underlying the invention that ribonuclease, in particular human ribonuclease 1, can cause podocyte regeneration, the corresponding targets of the ribonucleases can also be targeted. Using bioassays known to the skilled person in the art, the targets (receptors) of ribonuclease, in particular human ribonuclease, such as hRNase1, can be identified, for example, by binding experiments with labeled ribonucleases, in particular labeled hRNase1.

Consequently, it is also an object of the present invention to use pancreatic ribonuclease, in particular human pancreatic ribonuclease or hRNase 1 for the identification of ribonuclease receptors in an assay. In one embodiment, labeled ribonucleases (for example radioactive or fluorescent) may be used.

The identification of the corresponding targets or receptors of ribonuclease, in particular human pancreatic ribonucleases, can be of great therapeutic benefit, since knowledge of the receptor then enables the targeted development of low-molecular substances that simulate the effect of the high-molecular protein ribonuclease and can be used more easily for therapeutic purposes than the proteins themselves. Both antagonistically acting substances and agonistically acting substances can be identified.

Consequently, it is also an object of the present invention to use pancreatic ribonuclease, in particular human pancreatic ribonuclease or hRNase 1 to identify substrates of pancreatic ribonuclease that are causally related to podocyte degeneration.

FIG. 1: Phenotype of the PKCε-knockout. PKCε-deficiency causes glomerulosclerosis in mice and dysregulation of the actin cytoskeleton in murine podocytes.

A) Severe glomelurosclerosis and proteinuria develops from week 12 in PKCε-deficient mice.

B) Paxillin immunofluorescence staining visualizes focal adhesion molecules in podocytes. F-actin is visualized by phalloidin staining. Actin cytoskeletons are dysregulated in PKCε-deficient podocytes.

C) Image J was used to analyze the cell size. The cell size of PKCε-deficient podocytes is much smaller than that of wild-type podocytes.

D) The number of focal adhesion molecules in PKCεdeficient podocytes is also significantly smaller than that in number in wild-type podocytes.

FIG. 2: Fractions containing hRNase1 ameliorate actin cytoskeleton dysregulation in PKCε-deficient podocytes. PKCε-deficient podocytes are treated with different fractions isolated from hemofiltrate containing hRNase1. After 24-hour incubation, podocytes are fixed and stained with immunofluorescence. A) PKCε-deficient podocytes show the phenotype with small cell size and dysregulated actin cytoskeleton. B) The fraction E6F15S is able to improve the phenotype. Both the focal adhesion molecules and actin cytoskeleton can be visualized very well.

FIG. 3: Recombinant human RNAse 1 has a rescue effect on the cell structure of PKCε-deficient podocytes. The PKCε-deficient podocytes are incubated with recombinant human RNAse at different concentration for 24 hours. The rescue effect depends on the concentration of RNAse1. A slight rescue effect on PKCε-deficient podocytes can be shown from as low as 250 ng/ml. A) With increased concentration the rescue effect can be seen and up to 3000 ng/ml the effect reaches its maximum. B) Immunofluorescence staining shows the rescue effect with increased cell size and increase in focal contact density (top without RNAse, bottom with RNAse.

EXAMPLES

Bioassay

Determination of the Effect of Ribonuclease on Podocyte Modification.

Immortalized PKCε−/− podocytes (SV129 background) were seeded on coverslips in 24 well plates and differentiated for seven days prior to treatment. Recombinant human or bovine ribonuclease 1 was added to 400 µl of medium (RPMI 1046 medium containing 10% FCS and one percent penicillin/streptavidin) in each well and incubated for 24 hours at 37° C.

Podocytes treated in this manner were first fixed in 4% PFA for 10-15 min, then washed with PBS and stored in PBS at 4° C. Cells were permeabilized with 0.1% Triton X-100 for a period of 10 min and washed with PBS. Nonspecific antibody binding was blocked using 10% donkey serum for a period of 30 minutes at room temperature. Cells were then incubated with primary antibody (anti-paxillin antibody, clone 5H11, Cat. #05-417, Millipore) at 4° C. overnight or for 1 hour at room temperature. Unbound primary antibody was washed three times with PBS and incubated with corresponding secondary antibody and phalloidin (Alexa Fluor™ 555 Phalloidin, Cat. #A34055, Invitrogen) for 1 hour at room temperature. Cells were then washed again three times with PBS for 5 minutes. Briefly, coverslips were washed with double-distilled water, fixed on slides with Aquapolymout medium (containing DAPI), and stored at 4° C. Staining was visualized under a Leica DMLB microscope with a Leica DFC425C camera or under a Leica-2 confocal microscope.

The invention claimed is:

1. A medicament for use in the treatment or regeneration of functionally impaired glomerular podocytes, the medicament comprising an aqueous solution, a pharmaceutical excipient and a human pancreatic ribonuclease polypeptide having a sequence identity of 100% with SEQ ID No. 1, wherein the pharmaceutical excipient comprises a bacteriostatic agent, a surfactant comprising polysorbate 20, an isotonic agent comprising mannitol, a stabilizing amino acid effective to stabilize the polypeptide against aggregation or oligomerization, or a mixture thereof, and the medicament is a pharmaceutical composition formulated for parenteral administration.

2. The medicament of claim 1 wherein regeneration of the functionally impaired glomerular podocytes alleviates renal disease selected from the group consisting of diabetic nephropathy, nephrotic syndrome, nephritic syndrome, glomerular diseases such as membranous glomerulonephritis, focal segmental glomerulosclerosis (FSGS), IgA nephropathy, IgM nephropathy, membranoproliferative glomerulonephritis, minimal change disease, hypertensive nephrosclerosis and interstitial nephritis, Fabry disease, infections, aminoaciduria, Fanconi syndrome, heavy metal poisoning, sickle cell disease, haemoglobinuria, myoglobinuria, organ rejection, pre-eclampsia, acute renal failure and genetic podocytopathies.

3. The medicament of claim 1 wherein the medicament is formulated to deliver at least one human pancreatic ribonuclease polypeptide per dosage unit.

4. A method for treatment of a disease caused by functionally impaired glomerular podocytes by administering the medicament of claim 1 to a patient in need thereof.

5. The method of claim 4 wherein the disease is a renal disease selected from the group consisting of diabetic nephropathy, nephrotic syndrome, nephritic syndrome, glomerular diseases such as membranous glomerulonephritis, focal segmental glomerulosclerosis (FSGS), IgA nephropathy, IgM nephropathy, membranoproliferative glomerulonephritis, minimal change disease, hypertensive nephrosclerosis and interstitial nephritis, Fabry disease, infections, aminoaciduria, Fanconi syndrome, heavy metal poisoning, sickle cell disease, haemoglobinuria, myoglobinuria, organ rejection, pre-eclampsia, acute renal failure and genetic podocytopathies.

6. The medicament of claim 1 wherein the stabilizing amino acid is lysine and/or arginine.

7. The medicament of claim 1 wherein the polypeptide is labelled radioactively or fluorescently.

8. The medicament of claim 1 wherein a concentration of the polypeptide in the aqueous solution is from about 250 ng/ml to about 3000 ng/ml.

* * * * *

SEQUENCE LISTING

```
<160> NUMBER OF SEQ ID NOS: 3

<210> SEQ ID NO 1
<211> LENGTH: 127
<212> TYPE: PRT
<213> ORGANISM: human

<400> SEQUENCE: 1

Lys Glu Ser Arg Ala Lys Lys Phe Gln Arg Gln Met Asp Ser Asp Ser
1               5                   10                  15

Ser Pro Ser Ser Ser Ser Thr Tyr Cys Asn Gln Met Met Arg Arg Arg
            20                  25                  30

Asn Met Thr Gln Gly Arg Cys Lys Pro Val Asn Thr Phe Val His Glu
        35                  40                  45

Pro Leu Val Asp Val Gln Asn Val Cys Phe Gln Glu Lys Val Thr Cys
    50                  55                  60

Lys Asn Gly Gln Gly Asn Cys Tyr Lys Ser Asn Ser Ser Met His Ile
65                  70                  75                  80

Thr Asp Cys Arg Leu Thr Asn Gly Ser Arg Tyr Pro Asn Cys Ala Tyr
                85                  90                  95

Arg Thr Ser Pro Lys Glu Arg His Ile Ile Val Ala Cys Glu Gly Ser
            100                 105                 110

Pro Tyr Val Pro Val His Phe Asp Ala Ser Val Glu Asp Ser Thr
        115                 120                 125


<210> SEQ ID NO 2
<211> LENGTH: 155
<212> TYPE: PRT
<213> ORGANISM: human

<400> SEQUENCE: 2

Met Ala Leu Glu Lys Ser Leu Val Arg Leu Leu Leu Leu Val Leu Ile
1               5                   10                  15

Leu Leu Val Leu Gly Trp Val Gln Pro Ser Leu Gly Lys Glu Ser Arg
            20                  25                  30

Ala Lys Lys Phe Gln Arg Gln Met Asp Ser Asp Ser Ser Pro Ser Ser
        35                  40                  45

Ser Ser Thr Tyr Cys Asn Gln Met Met Arg Arg Arg Asn Met Thr Gln
    50                  55                  60
```

-continued

```
Gly Arg Cys Lys Pro Val Asn Thr Phe Val His Glu Pro Leu Val Asp
65                  70                  75                  80

Val Gln Asn Val Cys Phe Gln Glu Lys Val Thr Cys Lys Asn Gly Gln
                85                  90                  95

Gly Asn Cys Tyr Lys Ser Asn Ser Ser Met His Ile Thr Asp Cys Arg
            100                 105                 110

Leu Thr Asn Gly Ser Arg Tyr Pro Asn Cys Ala Tyr Arg Thr Ser Pro
        115                 120                 125

Lys Glu Arg His Ile Ile Val Ala Cys Glu Gly Ser Pro Tyr Val Pro
    130                 135                 140

Val His Phe Asp Ala Ser Val Glu Asp Ser Thr
145                 150                 155


<210> SEQ ID NO 3
<211> LENGTH: 28
<212> TYPE: PRT
<213> ORGANISM: human

<400> SEQUENCE: 3

Met Ala Leu Glu Lys Ser Leu Val Arg Leu Leu Leu Leu Val Leu Ile
1               5                   10                  15

Leu Leu Val Leu Gly Trp Val Gln Pro Ser Leu Gly
            20                  25
```